(12) United States Patent
Cuypers et al.

(10) Patent No.: US 11,944,507 B2
(45) Date of Patent: Apr. 2, 2024

(54) IMMOBILISATION DEVICE

(71) Applicant: Orfit Industries N.V., Wijnegem (BE)

(72) Inventors: Steven Cuypers, Schilde (BE); Bogdan Bogdanov, Schoten (BE)

(73) Assignee: Orfit Industries N.V., Wijnegem (BE)

( * ) Notice: Subject to any disclaimer, the term of this patent is extended or adjusted under 35 U.S.C. 154(b) by 885 days.

(21) Appl. No.: 16/964,639

(22) PCT Filed: Feb. 12, 2018

(86) PCT No.: PCT/EP2018/053430
§ 371 (c)(1),
(2) Date: Jul. 24, 2020

(87) PCT Pub. No.: WO2019/154521
PCT Pub. Date: Aug. 15, 2019

(65) Prior Publication Data
US 2021/0052344 A1     Feb. 25, 2021

(51) Int. Cl.
| | |
|---|---|
| A61B 90/18 | (2016.01) |
| A61L 31/04 | (2006.01) |
| A61L 31/14 | (2006.01) |
| B29C 51/00 | (2006.01) |
| C08J 5/18 | (2006.01) |
| C08L 67/04 | (2006.01) |
| C08L 75/06 | (2006.01) |
| B29K 96/00 | (2006.01) |
| B29L 31/00 | (2006.01) |

(52) U.S. Cl.
CPC ............ *A61B 90/18* (2016.02); *A61L 31/041* (2013.01); *A61L 31/14* (2013.01); *B29C 51/002* (2013.01); *C08J 5/18* (2013.01); *C08L 67/04* (2013.01); *C08L 75/06* (2013.01); *B29K 2096/00* (2013.01); *B29L 2031/753* (2013.01); *C08J 2367/04* (2013.01); *C08J 2375/06* (2013.01); *C08J 2445/00* (2013.01); *C08J 2467/04* (2013.01); *C08J 2475/06* (2013.01); *C08L 2203/16* (2013.01); *C08L 2312/00* (2013.01)

(58) Field of Classification Search
None
See application file for complete search history.

(56) References Cited

U.S. PATENT DOCUMENTS

| | | | | |
|---|---|---|---|---|
| 3,836,593 A | * | 9/1974 | Streck | C08G 61/08 526/140 |
| 4,316,457 A | * | 2/1982 | Liegeois | A61L 15/12 427/179 |
| 5,584,800 A | * | 12/1996 | Scholz | A61L 15/07 602/8 |
| 2010/0000549 A1 | * | 1/2010 | Nieberding | B32B 5/18 128/845 |
| 2012/0271007 A1 | * | 10/2012 | Zhang | C08F 283/006 264/494 |
| 2015/0000679 A1 | * | 1/2015 | Cuypers | B29C 35/0805 264/494 |
| 2019/0239581 A1 | * | 8/2019 | Rat | A01K 13/007 |

FOREIGN PATENT DOCUMENTS

| | | | | |
|---|---|---|---|---|
| CN | 104804386 A | * | 7/2015 | ............. C08L 67/04 |
| EP | 0235500 A2 | | 9/1987 | |
| EP | 2492316 A1 | | 8/2012 | |
| EP | 2537882 A1 | | 12/2012 | |
| JP | 06192375 A | * | 7/1994 | ............. C08G 18/42 |

OTHER PUBLICATIONS

Machine translation of CN-104804386-A (no date).*
"TPU for Adhesives Product Range | Pearlbond® TPU | Pearlstick® TPU" by Lubrizol (Year: 2013).*
Technical Data Sheet for Pearlbond™ 520 by Lubrizol. (Year: 2018).*
Technical Data Sheet for Pearlbond™ 522 by Lubrizol. (Year: 2018).*
Machine translation of JP-06192375-A (no date).*
Examination Report and English translation for related Chinese patent application No. 201880089024.5, dated Nov. 26, 2021. 13 pages.
International Search Report and Written Opinion in corresponding International Patent Application No. PCT/EP2018/053430 dated Oct. 5, 2018. 8 pages.
Luna et al., "Effect of injection parameters on the thermal, mechanical and thermomechanical properties of polycaprolactone (PCL)", Journal of Elastomers and Plastics, 2021, vol. 53, 1045-1062.
Gianotti and Capizzi, "Thermodynamic Data for Some Even Trans Polyalkenamers", European Polymer Journal, 1970, vol. 6: 743-749.
Schaible et al., "Basic Study on the Evaluation of Thermoplastic Polymers as Hot-Melt Adhesives for Mixed-Substrate Joining", Open Journal of Applied Sciences, 2016, vol. 6: 579-592.

* cited by examiner

*Primary Examiner* — Michael J Feely
(74) *Attorney, Agent, or Firm* — Leason Ellis LLP

(57) ABSTRACT

The present invention relates to a template for a positioning, fixation, mobilization or immobilization device, wherein the template comprises a sheet of a thermoplastic material, wherein the thermoplastic material comprises between 3.0 and 95.0 wt. % of a poly-ε-caprolactone polymer, preferably a poly-ε-caprolactone homopolymer, and at least 5.0 wt. % of at least one second polymer material with a melting temperature of between 40 and 85° C., wherein the at least one second polymer material is selected from the group of one or more of a polyalkenamer or a thermoplastic linear polyurethane which contains as a polyol a poly ε-caprolactone or a polyester polyol, wherein the poly-ε-caprolactone polymer and the second thermoplastic material are cross-linked.

18 Claims, No Drawings

IMMOBILISATION DEVICE

CROSS-REFERENCE TO RELATED PATENT APPLICATIONS

This application is a U.S. National Stage Application under 35 U.S.C. § 371 of International Patent Application No. PCT/EP2018/053430, filed Feb. 12, 2018, which is incorporated by reference in its entirety. The International Application was published on Aug. 15, 2019, as International Publication No. WO 2019/154521 A1.

The present invention relates to a template for a positioning, fixation, mobilization or immobilization device or for an element for positioning, fixing or mobilising one or more body parts of a living subject in a predetermined position and/or posture, wherein the template comprises a sheet of a thermoplastic material, according to the preamble of the first claim.

The present invention also relates to a method for manufacturing such a template, to an immobilisation device comprising such a template and to the use of such templates for the immobilisation of one or more parts of a body of a living subject.

Fixation and immobilization devices employing sheets of thermoplastic poly-ε-caprolactone find use in numerous medical applications such as in rehabilitation and orthopedics, in the immobilisation and mobilisation of injured ligaments, muscular or bone structures in general as well as in predetermined positions and/or postures. In this type of applications, often, the body part to be immobilised or mobilised is enclosed in the fixation or immoblisation device in a desired posture and/or position.

Other medical applications include the use of immobilisation devices for the immobilisation of one or more body parts in diagnostic methods or in the treatment of trauma or diseases. In this type of applications, the patient is usually supported in a prone or supine position on a patient couch associated with the diagnostic or treatment instrument, for example for magnetic resonance imaging (MRI), computer tomography (CT), external beam radiation therapy (EBRT), proton and Auger therapy, IMRT, stereotactic radiation, linear accelerator radiotherapy, etc without however being limited thereto. Some of the instruments used in those applications employ a patient couch in combination with an immobilisation device and a cushion for supporting for example the back of the patient's head and contiguous portion of the neck. The cushion may for example be pre-contoured into a specific shape or be shaped to conform to the back of the patient's head. The immobilisation device, when fastened to the patient couch, ensures that the relevant portion of the patient's body is held stationary or immobilised, at a predetermined position in a predetermined posture. An adequate positioning and immobilization of the part of the body targeted by the treatment is crucial, to ensure that radiation is directed to the body part to be treated and that the risk to irradiation of surrounding tissue may be reduced to a minimum. A reproducible positioning is of utmost importance in those therapies employing fractionated treatment, involving several treatment sessions spread over a period of weeks or months.

An important application field for immobilization devices relates to patient positioning, patient supporting and immobilisation in radiation therapy, diagnostic imaging and related therapies. Poly-ε-caprolactone sheets are particularly suitable for producing immobilisation devices for use with these instruments, because of their ability to be directly moulded onto the body and the body part that needs immobilisation. The immobilisation device is often made of a perforated sheet of poly-ε-caprolactone, but depending on the nature of the application, the sheet or template may also used in a non-perforated form. Although the immobilisation device fulfils the main function of holding the body part stationary, for example the patient's head, it is important that some comfort is provided to the patient and that the patient can breath properly and observe the environment through the perforations. The immobilisation device can be pre-formed to a shape that will generally conform to the contours of the targeted body part and later on be personalised in shape and dimensions to a certain patient, or it may be directly molded on the targeted body part to conform to the contours thereof as closely as possible. A frequently used immobilisation device is a personalised mask that is positioned over the face and/or head of a patient, but devices for the immobilisation of any other body parts of a patient exist as well.

The molding of the immobilisation device in order to achieve that it conforms to the shape and dimensions of the body part to be immobilised, for example the head or face, is typically carried out preceding the first treatment. After having been molded, a thus molded immobilisation mask can be mounted on the head of the patient and be fixed to the patient support table to place the patient's head in a desired position and hold it stationary in that position.

When molding the immobilisation device directly to the body part to be immobilised, for example as a mask to the patient's face and head, the perforated sheet or template is heated in order to achieve that the sheet becomes flexible and moldable and can be shaped into the desired form. The heated sheet or template is positioned to the face or head, shaped and stretched to conform to the contours of the face or head as close as possible, with the purpose of incorporating into the shape of the template many details of the face and head, such as for example nose-mouth-eyes-ears-protruding bones etc. This shaping typically takes some time, and therefore it is important that the material of the sheet or template keeps its flexibility and formability for a period of time which is sufficiently long to permit the necessary shaping to be carried out. Therefore, on the one hand the crystallisation rate of the template material should be sufficiently slow in order to have a sufficiently long molding time available for adequate, detailed molding of the template or sheet. On the other hand it is important that the molding time is sufficiently short and that the crystallisation rate of the thermoplastic material is sufficiently fast to reduce patient waiting times during cooling and hardening of the mask after the molding has been finished. Besides this, the direct shaping of the template not only involves positioning of the template on top of the body part, but it also involves a significant amount of stretching and moulding of the thermoplastic material around the body part while the thermoplastic material contacts the body part. This stretching and shaping is sensed by the patient as particularly unpleasant, frightening and claustrophobic.

After the moulding of the mask has been finished, the mask is left to cool and stiffen to a rigid structure with a desired positioning and fixation ability to hold the head, or any other body part stationary in a desired position.

Examples of the immobilization devices of the type discussed above are for example disclosed in EP1854439, EP1537831, EP1582187 in the name of Orfit Industries.

Poly-ε-caprolactone is a highly preferred material for use as a sheet material in the above-discussed applications, not only for its ability to be molded directly on a body part with the material adopting a low temperature that can be supported by the body, but also for its ability to be re-moulded when needed after having been moulded into a first shape. Poly-ε-caprolactone is further highly preferred for its high stability, rigidity and fixation force when the poly-ε-caprolactone is cooled and at least partly crystallised. With high fixation force is meant that as soon as having been immobilized by the immobilisation device, the ability for the immobilised body part to move or reposition within the immobilisation device, is limited to less than a few mm, preferably up to 1-2 mm or even less.

However, the crystallisation rate of poly-ε-caprolactone from the molten state is fast, so that a relatively short time remains available for molding the molten poly-ε-caprolactone to the shape of the body part to be immobilised.

There is thus a need for a thermoplastic material which may be shaped into sheets or templates, which is suitable for use in positioning, fixation, mobilisation and immobilisation devices of the type described above and which shows a slower crystallisation rate, so that a longer period of time remains available for molding a sheet or template to the body part that needs to be immobilised.

This is achieved according to the present invention with a template, which shows the technical features of the characterising portion of the first claims.

Thereto, the template of the present invention for a positioning, fixation, mobilization or immobilization device, comprises a a sheet of a thermoplastic material, wherein the thermoplastic material comprises between 3.0 and 95.0 wt. % of a poly-ε-caprolactone polymer, preferably a poly-ε-caprolactone homopolymer, and at least 5.0 wt. % of at least a second polymer material with a melting temperature of between 40 and 85° C., wherein the second polymer material is selected from the group of one or more of a polyalkenamer or a thermoplastic linear polyurethane which contains as a polyol a poly ε-caprolactone or a polyester polyol, wherein the poly-ε-caprolactone polymer and the second thermoplastic material are cross-linked.

The thermoplastic material used in the present invention comprises a thermoplastic poly-ε-caprolactone polymer and at least one second thermoplastic polymer material. It is within the scope of the present invention that the thermoplastic material may contain besides the second thermoplastic material, further thermoplastic materials so as to obtain a thermoplastic material with desired properties. It is within the scope of this invention that the thermoplastic composition may contain any other preferred functional compounds such as a UV-initiator and a cross-linking accelerator and any other relevant compounds.

In general, the poly-ε-caprolactone polymer will be present in the thermoplastic material in a concentration of 3 wt. % up to 95.0 wt. %, preferably of 15 wt. % up to 90.0 wt. %, more preferably a concentration of 20 wt. % up to 85.0 wt. %, wherein wt. % is expressed with respect to the weight of the thermoplastic material.

Where the thermoplastic material additionally contains thermoplastic polyurethane, in general the thermoplastic polyurethane will be present in the thermoplastic material in a concentration of at least 5.0 wt. % up to 97.0 wt. %, preferably of at least 5.0 wt. % up to 90.0 wt. %, more preferably in a concentration of at least 10.0 wt. % up to 85.0 wt. %, most preferably in a concentration of at least 15.0 wt. % up to 80.0 wt. %, wherein wt. % is expressed with respect to the weight of the thermoplastic material.

Where the thermoplastic material additionally contains a polyalkenamer, the thermoplastic polyalkenamer will be present in the thermoplastic material in a concentration of at least 5.0 wt. % up to 20.0 wt. %, preferably a concentration of at least 7.5 wt. % up to 15.0 wt. %, wherein wt. % is expressed with respect to the weight of the thermoplastic material.

The inventors have observed that by partially substituting poly-ε-caprolactone with another thermoplastic material with a melting temperature of between 40 and 85° C., in particular a polyalkenamer or a thermoplastic linear polyurethane which contains as a polyol a polyester polyol or a poly ε-caprolactone polyol, a thermoplastic material may be obtained with a slower crystallisation rate.

The inventors have observed that a partial substitution of the poly-ε-caprolactone by the second thermoplastic material described above may slow down the crystallisation rate, prolong the period before which crystallisation starts and increase the time available for molding the thermoplastic material to such an extent that a longer period of time remains available for the shaping of the sheet of thermoplastic material or the template to the contours of the body part to be immobilised and to which the template is to be applied. On the other hand it has been observed that the time period after which crystallisation starts is increased to a certain extent only and still remain sufficiently short to not prolong the waiting time for a patient to such an extent that it would become uncomfortable. In particular, the inventors have observed that the period of time which remains available for the molding of the thermoplastic material, and thus the point of time from which crystallisation starts, may be increased to at least 1 minute, in particular at least 1.5 minutes or at least 2 minutes, sometimes more than 2.5 minutes. In general, the molding time available, will not be longer than 15 minutes, preferably the available molding time will not be longer than 12.5 minutes, in particular it will not be longer than 10 minutes or maximum 5 minutes as this would again reduce the comfort to the patient due to an increasing cooling and waiting time.

Varying the degree of substitution of poly-ε-caprolactone in the blend according to the present invention as described above, permits controlling the crystallisation rate, the time available before crystallisation sets on and the time available for the molding of the thermoplastic material to at least a certain extent. Therefore, with more complicated shapes a larger degree of substitution of the poly-ε-caprolactone may be selected, whereas in situations where a high fixation force is preferred a smaller degree of substitution may be preferred.

Whereas poly-ε-caprolactone shows a distinctive shrinking upon cooling and crystallisation, a partial substitution of the poly-ε-caprolactone by the second thermoplastic polymer as claimed has been found to reduce shrinking of the thermoplastic material after the template has been shaped to the patient and has been left to cool and crystallise, and thereby to improve patient comfort during subsequent wearing of the immobilisation device produced from the template. Varying the degree of substitution of poly-ε-caprolactone in the thermoplastic material according to the present invention therefore permits controlling the degree of shrinkage of the template, in the course of time, after molding into an immobilisation device has been carried out.

Using for the thermoplastic material of the template a blend comprising poly-ε-caprolactone and at least one second thermoplastic polymer material will further have the effect that the elastic modulus and elasticity in the molten or softened state of the thermoplastic material may be controlled and may be improved, that toughness and rigidity of the thermoplastic material after cooling and crystallisation may be reduced, and that the haptics of the thermoplastic material evolve towards a more rubbery feeling instead of the hard touch provided by poly-ε-caprolactone alone, thereby improving comfort to the patient.

The at least one second thermoplastic material substituting for the poly-ε-caprolactone in the present invention is purposively selected because of its glass transition temperature, its melting temperature or melting range which should not be too far removed from that of poly-ε-caprolactone, to ensure a uniform softening or melting of the thermoplastic material as a whole, i.e. the poly-ε-caprolactone and the at least one second thermoplastic material, at a temperature that can be supported by the human and/or animal body.

In a preferred embodiment of this invention the poly-ε-caprolactone is a poly-ε-caprolactone homopolymer. Particularly preferred is a poly-ε-caprolactone with a number average molecular weight $M_n$ of at least 10.000 g/mole, more preferably at least 20.000 g/mole, most preferably at least 40.000 g/mole, in particular at least 50.000 g/mole. Poly-ε-caprolactone with a molecular weight below 10.000 g/mole will generally result in thermoplastic materials after crystallisation which are brittle. With further decreasing molecular weights, the poly-ε-caprolactone may become paste like or even liquid like, so that handling of the material risks to be compromised. Therefore, the poly-ε-caprolactone used in the template of this invention will generally have a number average molecular weight $M_n$ of maximum 100.000 g/mole, preferably maximum 90.000 g/mole. Poly-ε-caprolactone with a molecular weight above 100.000 g/mole may lead to slower crystallisation rates and reduce the moldability of the thermoplastic material in the molten state, thereby compromising the ability of the material to be shaped in the molten state and adversely affecting patient comfort. Poly-ε-caprolactones with varying molecular weights are commercially available from the company Perstorp UK Limited under the trade designation CAPA.

In the present application, the molecular weight Mn can be based on an end-group (hydroxyl number according to DIN 53240-1: 2013-06 or NCO content in accordance with EN ISO 1 1909), or by gel permeation chromatography (GPC) according to DIN 55672-1: 2007-08 determined using THF as eluent. Unless otherwise indicated, the molecular weights listed are those that have been determined by GPC. The weight average molecular weight Mw can also be determined by means of GPC, as indicated above.

Selection of the appropriate molecular weight will permit controlling the degree of crystallinity of the poly-ε-caprolactone after crystallisation. In practice the crystallinity of poly-ε-caprolactone has been found to decrease with an increasing number average molecular weight $M_n$. Poly-ε-caprolactones with a number average molecular weight $M_n$ in the mentioned ranges and appropriate degree of cross-linking have been found capable of enhancing the strength of the template after having been moulded to an immobilization device, and at the same time allowing for a desired and/or needed viscosity which is sufficiently high to permit handling, shaping, stretching and otherwise shaping of the thermoplastic material of the template when heated and softened.

Particularly preferred is poly-ε-caprolactone having a melt-flow index, measured with a 1" PVC die, 2.16 kg weight, for 600 sat 160° C. of at least 5.0 g/10 minutes, preferably at least 7.0 g/10 minutes.

Particularly preferred is further poly-ε-caprolactone having a melting temperature of between 40 and 75° C., preferably between 50 and 70° C., more preferably between 55 and 65° C., as these temperatures may be supported by the human and animal body and permit direct molding of the template to the body.

The poly-ε-caprolactone used in the thermoplastic material of the template of the present invention preferably contains between 35 and 70 wt. % of crystalline poly-ε-caprolactone, preferably between 40.0 and 65.0 wt. %, more preferably between 55.0 and 60.0 wt. %. Herein wt. % refers to the weight of crystalline poly-ε-caprolactone with respect to the total weight of the poly-ε-caprolactone contained in the thermoplastic material.

Suitable polymers for use as the at least one second thermoplastic polymer include thermoplastic linear polyurethanes, preferably those comprising a polyol which is a polyester polyol. More preferably use is made of thermoplastic linear polyurethanes wherein the polyol is a polyester polyol of a $C_4$-$C_{12}$ dicarboxylic acid and a polyol comprising diol building blocks with a $C_2$-$C_6$ hydrocarbon backbone. However, polyols with a longer hydrocarbon backbone may be used as well. In particular, the polyester polyol is a polyethylene or a polybutylene ester of one ore more di-carboxylic acids selected from the group of adipic acid, azeleic acid, sebacid acid or succinic acid, more preferably the polyester polyol is a polyethylene or a polybutylene ester of adipic acid. An appropriate selection of the diacids permits keeping the melting and glass transition temperature of the polyurethane sufficiently low, so that the polyester polyurethane is suitable for direct molding to the human or animal body, when mixed with a poly-ε-caprolactone as described above. Examples of polyester polyols, which can be used as a base of linear polyurethanes are commercially available under the name Fomrez®.

Where the thermoplastic linear polyurethane in the template of this invention is a poly-ε-caprolactone based polyurethane, the poly-ε-caprolactone units preferably have a number average molecular weight $M_n$ of maximum at least 1000 g/mol, preferably at least 2000 g/mole, more preferably at least 2500 g/mole, most preferably at least 5000 g/mole, to achieve a sufficiently high strength and at the same allowing for desired and/or needed sufficiently high viscosity when heated for being shaped. The poly-ε-caprolactone units preferably have a number average molecular weight Mn of maximum 10000 g/mole, preferably maximum 5000-g/mole, more preferably maximum 2500 g/mole, to ensure a sufficient flexibilty and elasticity when molten and permit shaping of the thermoplastic material. Selection of the appropriate molecular weight of the poly-ε-caprolactone polyol units will permit obtaining the preferred poly-ε-caprolactone based polyurethanes with a melting temperature of between 40 and 70° C., preferably between 50 and 70° C. and permits tuning stiffness, strength and ductility. Poly-ε-caprolactone based polyurethanes, with varying melting temperatures and onset of crystallisation temperatures are commercially available and the skilled person will be capable of identifying the poly-ε-caprolactone based polyurethane most appropriate for the intended application.

The di-isocyanate component of the polyester and poly-ε-caprolactone polyol based thermoplastic linear polyurethanes used with the present invention may be any di-isocyanate considered suitable by the skilled person. Examples of suitable di-isocyanates include those having a molecular weight of below 1000 g/mol, for example 4,4'-, 2,4'- and 2,2'-diphenyl-methane diisocyanate and any desired mixtures of these isomers (MDI), 2,4- and 2,6-tolylene diisocyanate and any desired mixtures of these isomers (TDI), 1,6-hexamethylene diisocyanate (HDI), 1-isocyanato-3,3,5-trimethyl-5-isocyanatomethylcyclohexane (i.e. isophorone diisocyanate or IPDI) and perhydro-2,4'- and -4,4'-diphenylmethane diisocyanate (HMDI). Other suitable di-isocyanates include 1-isocyanato-3,3,5- trimethyl-5-isocyanatomethylcyclohexane (i.e. isophorone diisocyanate or IPDI) and perhydro-2,4'- and -4,4'-diphenyl-methane diisocyanate (HMDI), preferably of 4,4'-, 2,4'- and/or 2,2'-diphenyl-methane diisocyanate (MDI).

Diphenyl-methane diisocyanate (MDI) is particularly preferred for use with the present invention because of the good tensile strength and high crystallinity provided. Usually it will be available as a mixture of 4,4'-, 2,4'- and 2,2'-diphenyl-methane diisocyanate. Nevertheless, 1,6 hexamethylene diisocyanate (HDI) may provide a good alternative for the higher elastic modulus provided and the higher flexibility offered. In stead of elastic modulus, the synonyms E-modulus or modulus of elasticity may be used as well.

The molar ratio of the di-isocyanate with respect to the polyester polyol and poly-ε-caprolactone polyol in the thermoplastic linear polyurethanes may vary within some ranges, but preferably varies from 1:3 to 1:2, and is more preferably about 1:1 to permit obtaining a thermoplastic sheet with optimal rigidity even after re-melting.

The crystallinity of the linear polyurethane can be influenced by the length of the soft polyester and/or poly-☐-caprolactone segments and the amount of hard di-isocyanate segment. A more stiff polyurethane molecular structure performs well with poly-☐-caprolactone or polyester diol of low molecular weight, whereas a more flexible polyurethane performs better with high molecular weight poly-☐-caprolactone/or polyester segments.

A preferred embodiment of this invention is characterised in that the sheet of thermoplastic material comprises a poly-☐-caprolactone based polyurethane or a polyester polyol polyurethane or a mixture of poly-☐-caprolactone polyol and polyester polyol, with a molding time of between 1 and 10 minutes, preferably between 1 and 5 minutes. In practise this means that crystallisation of the material will initiate after a period of time which varies from 1 to 10 minutes, preferably from 1 to 5 minutes.

The molding time, in other words the time available for molding of the thermoplastic material which generally corresponds to the period of time after which crystallization starts, has been found to also depend on and to vary with the thickness of the sheet of thermoplastic material, and the degree and type of perforation. Therefore in the present invention, preferably a sheet of thermoplastic material will be used with a thickness of between 1.2 and 4 mm preferably between 1.5-2.4 mm, more preferably between 1.6 and 3.2 mm. Further, preferably a sheet of thermoplastic material will be used with a degree of perforation between 1 and 25%, wherein % means the % of the surface of the thermoplastic sheet occupied by perforations, in relation to the total surface of the thermoplastic sheet.

The linear thermoplastic polyurethanes described above are preferred because of their melting temperature which is close to that of the poly ε-caprolactone, so that upon heating to the melting temperature of the poly ε-caprolactone which will often correspond to the temperature at which the template will be shaped to the body, a more or less uniform melting of the material may be obtained. The linear thermoplastic polyurethanes described above are further preferred because of their crystallisation rate, which is somewhat slower than that of poly ε-caprolactone homopolymer. As a result the time available for molding of the template to the body part to be immobilised may be prolonged. Typical molding times available for the molding of a non-perforated template or sheet made of a thermoplastic material consisting of poly ε-caprolactone and polycaprolactone polyurethane are 2-5 minutes.

Other suitable polymers for use as a second thermoplastic polymer include thermoplastic polyalkenamers. Polyalkenamers are well known in the art and they are commercially available from for example Evonik Industries. They are preferred for use in the present invention for their crystallinity, their melting temperature which is not too far removed from the melting temperature of poly-ε-caprolactone, and their ability to be cured using the processes suitable for curing poly-ε-caprolactone.

Particularly preferred polyalkenamers are polyoctenamers, i.e. polymers produced from cyclooctene, because of their melting temperature, their easy molding properties similarly to poly-ε-caprolactone, in combination with a sufficiently long molding time. The polyoctenamer used in the present invention may comprises cyclic macromolecules, linear macromolecules, or mixtures thereof. The average molecular weight of the polyoctenamer will generally range between 10.000 g/mole and 300.000 g/mole, preferably between 80.000 and 120.000 g/mole.

Preferred polyoctenamers are those having a melting temperature ranging between 5 and 80° C., preferably between 20° C. and 70° C., more preferably between 30° C. and 65° C., most preferably between 50° C. and 60° C. The polyoctenamer with the desired melting temperature may be obtained by an appropriate selection of the molecular weight and the content of trans isomer at the double bond at every eighth carbon atom in the ring.

In a preferred embodiment, the polyoctenamer has a degree of crystallinity of between 5 and 50%, preferably from 10 to 40%, more preferably from 25 to 35%. Herein % is expressed as the weight of crystalline polyoctenamer with respect to the total weight of polyoctenamer. The desired degree of crystallinity may be obtained by selecting the appropriate ratio of cis double bonds to trans double bonds in the polymer. In general, the crystallinity will increase as well as the melting temperature with increasing content of trans-bond polyoctenamer in comparison to cis-bond polyoctenamer.

Polyalkenamers may be cured and cross-linked using a conventional curing and cross-linking process such as those described below.

Cross-linking of the poly ε-caprolactone and the second thermoplastic material may be achieved using any of the suitable techniques known to the skilled person to achieve chemical cross-linking, which permit to control the degree of cross-linking and the mechanical properties of the polymer sheet after cross-linking has been carried out. A higher degree of cross-linking usually leads to a thermoplastic polymer sheet with a higher toughness and rigidity, a higher elastic modulus in the molten state and less plasticity, which is undesirable as it renders the moldability of the template much more difficult.

In this respect it is of great importance that the immobilization element exhibits a high stability, by which is meant that the ability to move or reposition the body part, once immobilized, is limited to less than a few mm, preferably up to 1-2 mm or even less.

Suitable techniques to achieve chemical cross-linking include cross-linking using a peroxide compound—in which case cross-linking may be initiated by heating the thermoplastic composition, and cross linking by exposing the thermoplastic sheet to irradiation, for example UV radiation, electron beam irradiation, or γ-radiation, but any other technique considered suitable by the skilled person may be used as well. γ-radiation cross-linking is usually carried out in devices, especially provided for that purpose, normally not present at the production site of the template, thereby making the production process slow and complex and inflexible. When use is made of γ-radiation in general an energy dose γ-radiation of between 1 and 100 KGy will suffice to achieve the desired degree of chemical cross-linking, preferably between 1 and 60, more preferably between 1 and 50 Kgy.

An advantageous technique of a preferred embodiment of this invention to achieve chemical cross-linking involves subjecting the thermoplastic material to UV radiation. This type of cross-linking presents the advantage that it may be carried out on each individual template or sheet, on-site where the template is produced or intended for use. Because of the smaller energy provided by a UV source, UV radiation permits to easily control the degree of cross-linking, taking into account the intended application.

In particular UV irradiation crosslinking offers the possibility to divide the template into zones, and to subject different zones to a different degree of cross-linking. A particular embodiment of the present invention is therefore characterized in that the template of thermoplastic material comprises at least a first and a second zone, wherein the first and second zone have a different degree of cross-linking.

Where UV cross-linking is envisaged, the thermoplastic material will preferably comprise a UV-cross-linking initiator in an amount which permits to achieve the desired degree of cross-linking. The most favourable concentrations and ratios may be determined empirically by varying the composition and subjecting the thermoplastic material to cross-linking. In general, the concentration of the UV-cross-linking initiator will vary between 0.1 and 10.0 weight %, and preferably between 0.2 and 5.0 weight %, based on the weight of the thermoplastic material.

Suitable UV-cross-linking initiator may be selected from the group of benzoin, substituted benzoins such as benzoin ethyl ether, benzophenone, benzophenone derivatives, Michler's ketone alfa-hydroxyketone, benzil dimethyl ketal, isopropyl thioxanthane, dialkoxyacetophenones such as diethoxyacetophenone, acetophenone, benzil, and other derivatives and mixtures thereof. Benzophenone is particularly preferred.

Where UV cross-linking is envisaged, the thermoplastic material will preferably also comprise a UV-cross-linking accelerator. Suitable UV-cross-linking accelerators are preferably polyfunctional, that is to say that they have two or more reactive functional groups which, when activated, are capable of forming a covalent bond with a functional group or free radicals on the polymer. UV-cross-linking accelerators with a low melting temperature (<100-120° C.) and a good compatibility with polycaprolactone and the linear thermoplastic polyurethane may be selected from the group of polyfunctional vinyl or allyl compounds such as triallyl cyanurate, triallyl isocyanurate, pentaerthritol tetramethacrylate, ethylene glycol, dimethacrylate, diallyl maleate, dipropargyl monoallyl cyanurate, isooctyl acrylate, 1,6-hexanediol diacrylate, neopentyl glycol diacrylate, trihydroxymethyl propane triacrylate, pentaerythritol triacrylate, dipentaerythritol hexaacrylate and other derivatives and mixtures thereof. The concentration of the UV-cross-linking accelerator may be varied within wide limits, but preferably ranges between 0.01 and 2.0 weight %, based on the weight of the thermoplastic material.

The thermoplastic sheet of the present invention may be perforated or not. The size, shape and positioning of the perforations, and the degree of perforating of the material may be as described above. The method of applying such perforations to thermoplastic sheets for use in immobilization devices for use in radiation therapy or diagnostic imaging etc. is well known to the skilled person. In general, in view of optimizing the time available for molding of the template, the degree of perforation of the thermoplastic sheet will vary between 1 and 25%, wherein % means the % of the surface of the thermoplastic sheet occupied by perforations, in relation to the total surface of the thermoplastic sheet.

The thermoplastic material may further contain one or more nano materials, in particular nano clay and/or nano carbon, more in particular carbon nano tubes. Within the scope of this invention organo-modified nano clay and both multi-walled and single-walled carbon nanotubes can be used.

Preferably, the carbon nanotubes are multiwall carbon nanotubes as they are easier to produce than single-walled carbon nanotubes, which clearly reduces cost. Where necessary, the surface of the nanotubes may be modified to improve compatibility with and dispersion in the thermoplastic material. Surface modifications may for example involve surface oxidation or modification of the carbon nanotubes with organic functional groups, compatible with the thermoplastic material into which the nanotubes are to be dispersed. Surface modification may also comprise grafting on the surface of the carbon nanotubes poly-ε-caprolactone or other thermoplastic material as described above.

The dimensions of the carbon nanotubes can vary within wide limits. In the case of multi-walled carbon nanotubes, they preferably have an inner diameter of 0.5-15 nm, preferably 3-7 nm, an outer diameter of 1-50 nm, preferably 5 to 25 nm, and a length of up to 100 μm, preferably a maximum of 75 micron, more preferably up to 50 micron. Dispersion of carbon nanotubes in the thermoplastic material may be achieved by dispersing them a in dispersing liquid in which the thermoplastic polymer does not dissolve, exposing the dispersion to ultrasonic waves, adding particles of thermoplastic polymer to the dispersion, mixing the dispersion to achieve removal of the dispersing liquid, forming the thermoplastic material into sheets as described below. The concentration of carbon nanotubes will usually be lower than 2.0 wt. %, preferably lower than 1.5 wt. %, more preferably lower than 1.0 wt. %. The minimum concentration of the carbon nanotubes will usually be at least 0.05 wt. %, preferably greater than 0.1 wt. %, more preferably greater than 0.25 wt. %.

Another preferred embodiment of this invention is characterised in that the thermoplastic material contains between 1 and 15 wt. % of one or more types of organically modified clay as a layered, lamellar nano mineral, preferably between 2 and 10 wt. %, more preferably between 3 and 5 wt. % with respect to the weight of the thermoplastic material. Within these ranges optimum exfoliation of the nano clay particles and uniform dispersion in the thermoplastic material can be achieved. At concentrations below 1 wt. % the effect on the flexural modulus decreases. At concentrations above 10 wt. % the viscosity of the mixture thermoplastic material—clay nano filler increases to values where the mixture becomes more and more difficult to handle and-process, the transparency to X-rays decreases.

Within the scope of this invention a melt mixing of polymer nano composite materials based on nanoclay and/or carbon nano tubes can be optimised by using twin screw extruder with suitable screw configuration.

Cross-linking of the thermoplastic material of the present invention may be carried out in advance of applying the perforations to the sheet of thermoplastic material or thereafter. The skilled person may prefer to carry out cross-linking of the thermoplastic material shortly before moulding of the template into a desired shape, in order to be able to control the degree of cross-linking depending on the intended use. The skilled person may prefer to partially cross-link the thermoplastic material after it has been shaped into a sheet, and to carry out a second cross-linking before the template is shaped into an immobilisation device. Crosslinking using UV irradiation or by heating of suitable incorporated peroxide may be particularly suitable in this case.

The present invention also relates to a preform comprising a template as described above, that has been moulded into a desired shape. In order to minimize time consumption, the template of this invention may be moulded to a certain degree to take the shape of any body part. Thereby it may be envisaged to have the preform available in a variety of sizes. The preform may be made of a sheet of thermoplastic material that has been perforated or not. The preform may have been subjected to cross-linking, or it may have been treated in such a way that a partial cross-linking of the thermoplastic material is achieved, with the purpose of further cross-linking the template before it is shaped into an immobilization device. The pre-molded/preformed templates in a variety of sizes can be partially heated to the soften stage and finally molded on the exact body part.

The present invention also relates to the use of a sheet of thermoplastic material for the production of a template as described above, wherein the thermoplastic material comprises between 3.0 and 95.0 wt. % of a poly-ε-caprolactone polymer, preferably a poly-ε-caprolactone homopolymer, and at least 5.0 wt. % of a second polymer material with a melting temperature of between 40 and 85° C., wherein the second polymer material is selected from the group of one or more of a polyalkenamer or a thermoplastic linear polyurethane which contains as a polyol a poly ε-caprolactone or a polyester polyol, wherein the poly-ε-caprolactone and the second thermoplastic material are cross-linked.

The present invention additionally relates to an immobilisation device comprising a template as described above, in a shape that permits immobilization of a desired body part.

The present invention further relates to a method for producing a template as described above, according to which 3-95.0 wt. % of a thermoplastic poly-ε-caprolactone polymer is blended with at least 5.0 wt. % of a second thermoplastic material with a melting temperature of between 40 and 85° C., which is selected from the group comprising one or more of a polyoctenamer and a thermoplastic linear polyurethane, wherein the thermoplastic linear polyurethane comprises a polyol which is a poly ε-caprolactone or a polyester polyol, wherein the thus obtained blend is heated to melt the material, and moulded into a sheet.

A preferred embodiment of this invention is characterised in that the additionally 0.2-5.0 weight %, based on the weight of the thermoplastic material of a cross-linking activator is blended with the thermoplastic material, and in that the thermoplastic material is subjected to UV irradiation cross-linking.

A further preferred embodiment is characterised in that the thermoplastic material is subjected to cross-linking after having been shaped into a sheet. A still further preferred embodiment is characterised in that the thermoplastic material is subjected to cross-linking after having been shaped into a template.

A preferred embodiment is characterised in that cross-linking is achieved by irradiation of the template with an energy dose of between 1 and 100, preferably between 1 and 60 Kgy, more preferably between 1 and 50 KGy.

A further preferred embodiment is characterised in that the template is perforated in advance of being subjected to cross-linking.

The present invention additionally relates to a method for producing an immobilisation device, wherein a template as described is heated to a temperature between 40 and 85° C., preferably between 40 and 70° C., more preferably between 50 and 70° C., most preferably between 55 and 65° C., positioned on the body part that needs to be positioned, mobilised or immobilised, shaped to conform to the contours of the body part and left to cool. The step of shaping of the template may if so desired, be preceded on site by a step of cross-linking the thermoplastic material, or according to a different embodiment cross-linking of the thermoplastic material may be carried out in advance of moulding or shaping of the template.

The invention is further illustrated in the examples below.

In the examples below the flexural modulus (MPa) was measured using the method described in ASTM D790. The time of isometric crystallization was determined according to the method disclosed in BE1015081.

EXAMPLE 1 AND 2

Two blends were prepared of
- poly-ε-caprolactone (PCL) with a number averaged molecular weight Mn of about 50000 and a melting range of between 58 and 60° C.,
- and a polyoctenamer (POM) with a trans-double bond content of nearly 80%, a molecular weight of 90000, a melting point of 54° C., in the amounts indicated in the table 1 below.

The blend further contained 1.0 wt. % of triallyl isocyanurate as a cross-linking initiator. The triallyl isocyanurate was incorporated into the PCL and its amount is included in the amount of PCL in table 1.

The blend was mixed in a twin screw extruder at 130° C., cooled and formed into granules. An amount of granules was heated to a temperature of 130° C. and press molded into a thermoplastic sheet with a thickness of 2.0 mm and a size of 250×250 mm, using an hydraulic press of Agila model PE30.

The thermoplastic sheet was subjected to cross-linking by subjecting it to irradiation doses of 5 KGy. The properties of the cross-linked sheet are summarized in Table 1 below.

TABLE 1

| | | | Time of isometric crystallisation | | | 3-Point-Bending |
|---|---|---|---|---|---|---|
| Ex. | PCL wt. %* | POM wt. % | Crystallistion onset* | 50% crystallisation* | Full crystallisation** | Max. contraction load (N) | Flexural Modulus (MPa) |
| 1 | 95 | 5 | 2 m 15 s | 5 m 10 s | 19 m | 46.9 | 491 |
| 2 | 85 | 15 | 2 m 30 s | 5 m 45 s | 21 m | 42.18 | 444 |

*the poly-ε-caprolactone contained 1.5 wt. % of the usual additives
**in minutes (m) and seconds (s)

The memory, measured after reheating of samples which had been subjected to stretching, with a degree of stretching of 70% at 65° C., was almost 100% for each of the samples. This means that the samples which had been subjected to 70% stretching at 65° C., followed by cooling to room temperature in the stretched condition while being fixed to a support member, and which were thereafter reheated to 65° C., returned to their initial shape upon cooling—also when not fixed to a support member.

From table 1 it can be concluded that by incorporation of the polyoctenamer into the thermoplastic poly ε-caprolactone, the period of time which elapsed before crystallization started and that the time available up to full crystallization of the material, could be increased. As a result, more time remains available for the moulding of a sheet of thermoplastic material according to the invention, onto a body part to be immobilized, into a desired shape.

As can be understood from table 1, with an increasing degree of substitution of poly-ε-caprolactone, the material of the thermoplastic sheet was sensed by the test persons as softer to the skin.

EXAMPLE 3-4 AND COMPARATIVE EXAMPLE A

A blend was prepared of varying amounts of
poly-ε-caprolactone (PCL) with a number averaged molecular weight Mn of about 50000 and a melting range of between 58 and 60° C., and
a linear thermoplastic polyurethane (PU), which contained poly-ε-caprolactone units as a polyol with a melting range of 65-71° C.,
in the amounts indicated in the table 2 below. The blend further contained about 1 wt. % of triallyl isocyanurate as a cross-linking agent. The triallyl isocyanurate was incorporated into the PCL and its amount is included in the amount of PCL in table 1.

The blend was subjected to melt mixing with a twin screw extruder at 130° C., thereafter cooled and granulated. The thus obtained granules were heated to a temperature of 130° C., and press molded into a sheet with a thickness of 2.0 mm and a size 250×250 mm using an hydraulic press of Agila model PE30. The thermoplastic sheet was subjected to cross-linking by subjecting it to □-irradiation. of 5 KGy.

The properties of the cross-linked sheet are summarized in table 2 below.

From table 2 it can be concluded that by incorporation of polyurethane into the poly-ε-caprolactone, the time available up to the start of the crystallization, as well as the time available up to full crystallization of the material increased. As a result, more time remains available for the moulding of a sheet onto the body part to be immobilized, into a desired shape.

With an increasing degree of substitution of PCL, the material of the thermoplastic sheet was sensed by the test persons as softer to the skin.

TABLE 2

|  |  |  | Time of isometric crystallisation | |
|---|---|---|---|---|
| Ex. | PCL wt. % | PU wt. % | Crystallisation onset (min s) | Maximum contraction load (N) |
| A | 100 | 0 | 1 m 30 s | 50 |
| 3 | 90 | 10 | 2 m 00 s | 47 |
| 4 | 3 | 97 | 3 m 30 s | 22 |

\* the poly-ε-caprolactone contained 1.5 wt. % of the usual additives
\*\* in minutes (m) and seconds (s)

EXAMPLE 5-6

A 3 points fixation mask was cut from a perforated sheet that had been produced from the mixtures of polyoctenamer and poly-ε-caprolactone of example 1 and 2. The mask was heated to a temperature of 65° C. and molded on a dummy head. The fixation/shrinkage force Fv was measured during cooling of the mask after 30 min and 24 h by using the method described in a patent application BE 1015081. The results are presented in Table 3.

From Table 3 it can be concluded that by incorporation of the polyoctenamer the shrinkage force of immobilization mask decreased which will increases the comfort of the patient.

TABLE 3

|  |  |  | Mask - Shrinkage Force (Fv) | |
|---|---|---|---|---|
| Ex. | PCL wt. % | POM wt. % | Fv (30 min) (N) | Fv (24 hours) (N) |
| 5 | 95 | 5 | 123 | 190 |
| 6 | 85 | 15 | 110 | 163 |

\* the poly-ε-caprolactone contained 1.5 wt. % of the usual additives

EXAMPLE 7-8 AND COMPARATIVE EXAMPLE B

A 3 points fixation masks was cut from a maximally perforated sheet produced from a thermoplastic material that contained both poly-ε-caprolactone and a linear polyurethane with poly-ε-caprolactone diol. The mask was heated or activated at 65° C. and molded on a dummy head. The fixation/shrinkage force Fv was measured during cooling of the mask after 30 min and 48 hours. The measured test results are presented in Table 4.

TABLE 4

| Properties of 3 points fixation masks based on composition of PCL and PU. | | | | |
|---|---|---|---|---|
|  |  |  | Shrink and Stability | |
| Ex. | PCL wt % | PU wt. % | Fv (30 min) (N) | Fv (48 hours) (N) |
| B | 100 | 0 | 75 | 170 |
| 7 | 85 | 15 | 60 | 150 |
| 8 | 70 | 30 | 50 | 120 |

\* the poly-ε-caprolactone contained 1.5 wt. % of the usual additives

From Table 4 it can be concluded that by incorporation of the linear PU containing poly-ε-caprolactone diol, the shrinkage force Fv of the immobilization mask could be reduced, which will increases the comfort of the patient.

Then invention claimed is:

1. A template for a positioning, fixation, mobilization or immobilization device, wherein the template comprises a sheet of an at least partially cross-linked thermoplastic material, wherein the thermoplastic material comprises:
   between 3.0 and 95.0 wt. % of a poly-ε-caprolactone polymer, wherein the poly-ε-caprolactone polymer has a number average molecular weight Mn of at least 50.000 g/mole and of maximum 90.000 g/mole, and
   at least 5.0 wt. % of at least one second thermoplastic polymer material with a melting temperature of between 40 and 85° C., wherein the at least one second thermoplastic polymer material is one or more of a thermoplastic polyalkenamer or a thermoplastic linear polyurethane based on a poly-ε-caprolactone polyol or a polyester polyol;

wherein the poly-ε-caprolactone polymer and the second thermoplastic polymer material are cross-linked.

2. A template according to claim 1, wherein the poly-ε-caprolactone polymer is present in the thermoplastic material in a concentration of between 15.0 and 90.0 wt.

3. A template according to claim 1, wherein the thermoplastic linear polyurethane is present in the thermoplastic material in a concentration of between 5.0 and 97.0 wt. %.

4. A template according to claim 1, wherein the thermoplastic polyalkenamer is present in the thermoplastic material in a concentration of 5 wt. % up to 20.0 wt. %.

5. A template according to claim 1, wherein the poly-ε-caprolactone polymer has a melting temperature of between 40 and 70° C.

6. A template according to claim 1, wherein the poly-ε-caprolactone polymer contains between 35 and 70 wt. % of crystalline poly-ε-caprolactone with respect to the weight of the poly-ε-caprolactone polymer.

7. A template according to claim 1, wherein the poly-ε-caprolactone polyol units of the thermoplastic linear polyurethane have a number average molecular weight Mn of at least 1000 g/mole and maximum 2500 g/mole.

8. A template according to claim 1, wherein the thermoplastic linear polyurethane based on a poly-ε-caprolactone polyol has a melting temperature of between 40 and 70° C.

9. A template according to claim 1, wherein the thermoplastic material has a molding time of between 1 and 15 minutes after having been heated to the melting temperature.

10. A template according to claim 1, wherein the thermoplastic polyalkenamer is a polyoctenomer, having a melting temperature ranging between 5 and 80° C.

11. A method for producing a template according to claim 1, comprising:
preparing the thermoplastic material by blending the poly-ε-caprolactone polymer and the at least one second thermoplastic polymer material with a melting temperature of between 40 and 85° C.,
blending the thermoplastic material with a cross-linking initiator, wherein the cross-linking initiator is provided in an amount of 0.2-10.0 wt. % based on the weight of the thermoplastic material;
forming the thermoplastic material into a sheet; and
subjecting the sheet to cross-linking to at least partially cross-link the thermoplastic material.

12. A method according to claim 11, wherein the template is perforated in advance of being subjected to cross-linking.

13. A method according to claim 11, wherein cross-linking involves a first step of partial cross-linking of the thermoplastic material after it has been shaped into a sheet, and a second step of further cross-linking before the sheet of thermoplastic material is shaped into an immobilization device.

14. A method for shaping a template according to claim 1 to a part of a body of a living subject that needs to be positioned, mobilized or immobilized, wherein a thermoplastic material is heated to a temperature of between 40 and 85° C., positioned on the body part, shaped to conform to the contours of the body part, and left to cool.

15. An immobilization device comprising a template according to claim 1 molded into a shape that permits immobilization of a desired body part.

16. A method for producing an immobilization device, wherein a template according to claim 1 is heated to a temperature between 40 and 85° C., positioned on a body part that needs to be positioned, mobilized or immobilized, shaped to conform to the contours of the body part, and left to cool.

17. A sheet of an at least partially cross-linked thermoplastic material, wherein the thermoplastic material comprises;
between 3.0 and 95.0 wt. % of a poly-ε-caprolactone polymer, wherein the poly-ε-caprolactone polymer has a number average molecular weight Mn of at least 50.000 g/mole and a maximum 90.000 g/mole, and
at least 5.0 wt. % of at least one second thermoplastic polymer material with a melting temperature of between 40 and 85° C., wherein the at least one second thermoplastic polymer material is one or more of a thermoplastic polyalkenamer or a thermoplastic linear polyurethane based on a poly ε-caprolactone polyol or a polyester polyol;
wherein the poly-ε-caprolactone polymer and the second thermoplastic polymer material are cross-linked.

18. An immobilization device comprising a sheet according to claim 17 molded into a shape that permits immobilization of a desired body part.

* * * * *